United States Patent
Braun et al.

(10) Patent No.: US 7,169,757 B2
(45) Date of Patent: Jan. 30, 2007

(54) STABILIZING CGMP IN AQUEOUS FORMULATION

(75) Inventors: Marcel Braun, Konolfingen (CH); Peter Erdmann, Bern (CH)

(73) Assignee: Nestec S.A., Vevey (CH)

( * ) Notice: Subject to any disclaimer, the term of this patent is extended or adjusted under 35 U.S.C. 154(b) by 112 days.

(21) Appl. No.: 10/506,727

(22) PCT Filed: Jan. 16, 2003

(86) PCT No.: PCT/EP03/00411

§ 371 (c)(1),
(2), (4) Date: Oct. 18, 2004

(87) PCT Pub. No.: WO03/074017

PCT Pub. Date: Sep. 12, 2003

(65) Prior Publication Data

US 2005/0169998 A1  Aug. 4, 2005

(30) Foreign Application Priority Data

Mar. 4, 2002  (EP) ................................ 02004880

(51) Int. Cl.
*A61K 38/17* (2006.01)
(52) U.S. Cl. ........................................................ 514/12
(58) Field of Classification Search ..................... None
See application file for complete search history.

(56) References Cited

U.S. PATENT DOCUMENTS 4,530,906 A * 7/1985 Higashi et al. ............. 435/223
4,975,289 A  12/1990 Ameyama et al.
5,853,704 A * 12/1998 Zhang et al. .................. 424/52

FOREIGN PATENT DOCUMENTS

EP  0575121 A1 * 12/1993

* cited by examiner

*Primary Examiner*—Robert A. Wax
(74) *Attorney, Agent, or Firm*—Bell, Boyd & Lloyd LLC

(57) ABSTRACT

A cGMP containing aqueous composition exhibiting a reduced off-flavor even after extended storage, comprising a hydrophobic resin; and an agent, that chemically blocks functional groups in cGMP. Methods of preparing and using the product are also provided.

26 Claims, No Drawings

STABILIZING CGMP IN AQUEOUS FORMULATION

This application is a 371 of PCT/EP03/00411 filed on Jan. 16, 2003, which in turn claims priority to European application, 02004880.7 filed on Mar. 4, 2002.

BACKGROUND OF THE INVENTION

The present invention relates to a method of stabilizing caseino-glycomacropeptide (cGMP) in aqueous formulations and reducing an off-flavor formation. In particular, the present invention comprises a formulation, having a pH below about 0.6 and/or, comprising a hydrophobic resin and/or an agent blocking functional groups in the caseino-glycomacropeptide.

Caseino-glycomacropeptide (cGMP) is a glycosylated compound formed during the enzymatic cleavage of kappa-casein from the milk of mammals by the action of rennet or pepsin. To obtain this compound as a starting material, e.g. an acidic casein or a caseinate hydrolyzed by rennet, or even a demineralized, lactose-free sweet whey, is treated with trichloroacetic acid to precipitate the proteins, the supernatant is collected and dialyzed, and finally, the dialysate is dried.

So as to obtain cGMP on an industrial scale acidic casein or sodium or calcium caseinate is treated with rennet which results in the coagulation of para-kappa-casein. The supernatant is then acidified to a pH of about 4–5 in order to precipitate the calcium phospho-caseinate. After separation of the precipitate, the solution is neutralized, demineralized by reverse osmosis, and finally concentrated and dried. Other processes include flocculating whey proteins from whey emanating from cheese production, recovering the supernatant and ultrafiltrating the supernatant using membranes having a cutoff threshold of approximately 15,000 Dalton, thus producing a retentate containing the sialo-glycoproteins.

The cGMP thus obtained is utilized in a variety of different applications, such as in a supplement to nutritional formulas as anti-thrombotic, anti-diarrhoeal compound and for special amino acid diets. Due to its microbizidal activity cGMP is also utilized in formulations for treating bacteria in the buccal cavity which are responsible for the formation of dental plaque and caries. It has been found that the capacity of Actinomyces strains and Streptococcus strains, bacteria populating the buccal cavity and considered to be involved in the initiation and formation of dental plaque, to adhere to buccal epithelial cells, to the surface of teeth coated with saliva and to form co-aggregates with one another may be reduced by providing cGMP in dental formulations, thus diminishing the detrimental effects of said bacterial strains. In addition, cGMP is also described to participate in the effect of a remineralization of demineralized portions of tooth structures.

One of the disadvantages of such formulations, however, resides in that an off-flavor develops during storage thereof. To solve this problem the art has proposed to include binding proteins in the formulations, such as antibodies, as a means of controlling the perceptibility of odoriferous materials which may be present, more specifically undesirable flavors or fragrances or constituents thereof.

Yet, proceeding accordingly is still cumbersome and due to the materials involved also expensive.

SUMMARY OF THE INVENTION

An object of the present invention therefore resides in overcoming the shortcomings of the prior art and to provide a cGMP containing formulation, that exhibits an extended shelf life without developing off-flavor.

During the extensive studies leading to the present invention, the inventors achieved to solve this problem by providing a cGMP containing aqueous composition comprising, a hydrophobic resin and an agent, that blocks specific functional groups in cGMP, responsible for off-flavour formation, and/or by adjusting the pH of the composition to a value of less than about 7.

Surprisingly, an extension of the shelf-life of cGMP containing products may already be obtained by simply lowering the pH-value of the product below about 6. However, for many products, in particular for compositions which are intended to be used on the skin or in the orifice a higher pH-value is desirable. In order to be able provide also cGMP-containing products with a pH-value above about 6, having an extended shelf-life, the present invention proposes the addition of a hydrophobic resin and of an agent blocking the functional groups in cGMP.

Additional features and advantages of the present invention are described in, and will be apparent from, the following Detailed Description of the Invention.

DETAILED DESCRIPTION OF THE INVENTION

One of the main advantages of the present invention is that both, the addition of a hydrophobic resin and of an agent blocking the functional groups in cGMP and the lowering of the pH-value are complementing each other. Depending on the chosen final product and/or the desired shelf-life, a person skilled in the art may obtain stable products by tuning both, the pH-value and the amount of hydrophobic resin and blocking agent to be added. Thus, the present invention offers not only the possibility to stabilize the composition, but also to minimize the amount of the respective additives, by decreasing the pH of the product correspondingly. The minimization of food additives is very desirable both economically and in view of the acceptance of the product, as products having an low amount of food additives are highly estimated by the customers.

Additionally, the composition of the present invention not only exhibits an extended shelf-life, but surprisingly also provides an increased stability and an essentially reduced off-flavor formation, when exposed transiently during storage or transportation to temperatures above room-temperature.

In a second aspect the present invention provides a method of producing a composition, which comprises preparing a composition comprising cGMP, adding an agent, that chemically blocks functional groups in cGMP and a hydrophobic resin, and/or adjusting the pH-value to a value in the range of from about 3 to about 6.

In a third aspect the present invention provides use of the composition in the manufacture of a medicament or a composition for treating or preventing caries, plaque formation, dental diseases, diseases of the mouth cavity or gums.

Preferably, said hydrophobic resin may be selected from the group consisting of SERDOLITH® III polystyrene-divinylbenzene-copolymer resin, LEWATIT® EP-63 polystyrene-divinylbenzene-copolymer resin, LEWATIT® OC 1064 LEWATIT® ion exchange resin, LEWATIT® OC 1066 ion exchange resin, LEWATIT® VC-OC ion exchange resin or AMBERLITE® XAD polystyrene copolymer resin and combines thereof. In a preferred way, a food-tolerable substance is used instead of hydrophobic resin, such as chlorophillin, sodium octenyl succinate starch, hydroxypropyl methyl cellulose or casein. Without being bound to any theory it may be supposed that said hydrophobic resin is acting as a sorbens trapping certain off-flavor substances. The amount of the hydrophobic resin may be selected in the range of from 0.01 to about 5 wt.-%, preferably from 0.05 to about 5 wt.-%, more preferably from 0.1 to about 2 wt.-%, each based on the final product.

The blocking or masking agent may be chosen from any acid anhydride, that may be included in an aqueous formulation, or derivatives thereof. Preferred examples may be selected from the group consisting of succinic anhydride, maleic anhydride, propio-lactone, chlorophillin and derivatives thereof, such as there isomeric forms. In the context of this application the term "derivatives thereof" comprises any compound derived from the above mentioned components by e.g. substituting moieties, as long as the activated acid component, i.e. the anhydride element remains. When utilized in a food product the blocking agent is preferably a food-grade chemical compound. Without being bound to any theory, it is supposed that said acid anhydrides react with chemical moieties of cGMP, in particular with amino groups, and thus prevent e.g. Maillard reactions or Strecker degradation reactions. The amount of the blocking agent is in the range of from about 0.005 to 1 wt.-%, preferably 0.01 to 1 wt.-%, more preferably 0.01 to 0.6 wt.-%, more preferably 0.1 to 0.5 wt.-%, each based on the final product.

The pH of the final product or composition is in the range of from about 3 to about 7, preferably in the range of from about 4 to about 6. For an lowering of the pH-value organic or inorganic acids or acidic buffer systems may be used, in particular e.g. aqueous HCl, $H_3PO_4$ and acetic acid.

The composition contemplated by the present invention may be any aqueous formulation, preferably any composition having a water activity between 0.2–1, since in these formulations the detrimental effects of a degradation and/or off-flavor development are prominent. The invention is particularly suited for compositions having a water activity of between 0.7–0.9, more preferably of about 0.8. The term "water activity" is to be understood as defined in e.g. Food Chemistry, Belitz H. D., Grosch W., (1999) p. 4–6, Springer. The measurement of water activity was performed on a Hygroskop DT (Rotronic AG, Zurich, Switzerland).

In principle, the composition of the present invention may be any food or pharmaceutical product containing cGMP, in particular a food product having a sweet taste due to the presence of sugars or sugar substitutes, which tend to be involved in Maillard reactions (that result in an off-flavor of the product), dairy products, such as e.g. an infant formula or a pharmaceutical product, in particular a pharmaceutical product for treating or preventing dental problems, such as e.g. caries or plaque formation, or a cosmetic or an oral composition.

According to a preferred embodiment, the composition of the invention may be a product for oral hygiene or a product for any application in the mouth cavity and/or throat, in particular a tooth paste, a gel, a tooth powder, a mouth wash, a chewing gum, a tablet or a lozenge. In particular, the composition may also be a product for oral hygiene which is present in pre-applied form on any dental cleaning means, such as dental floss.

A preferred embodiment of the invention is a composition comprising cGMP, Serdolith 111, and succinic anhydride or maleic anhydride.

The following examples illustrate the invention in a more detailed manner. It has, however, to be understood that the present invention is not limited to the examples but is rather embraced by the scope of the appended claims.

EXAMPLE 1

Preparation of a cGMP Basis Composition

A cGMP basis composition consisting of 39 wt.-% glycerol, 10 wt.-% cGMP, 0.002 wt.-% chlorohexidine (in this model added as preservative against microbial growth) and water was prepared. The resulting basis composition has an water activity value $a_w$ of 0.8, which was determined according to manufacturer instructions (Hygroskop DT, Rotronic AG, Zurich, Switzerland).

EXAMPLE 2 pH-Dependent Off-Flavor Formation

Samples of the cGMP basis composition according to Example 1 were taken and the pH value of each of said samples was adjusted by adding either 1 M hydrochloric acid or 2 M sodium hydroxide to a pH-value in the range of between 5.5 and 8.0. All samples were stored at 49° C. for 3 weeks and were subjected subsequently to organoleptic tests.

No off-flavor was organoleptically detectable in samples having a pH-value of less than 6. During said organoleptic tests, test persons evaluated the odor of the samples adjusted to different pH-values.

These results were confirmed by a volatile flavor analysis by GC-MS. The volatile flavor compounds can be extracted according to the method described by De Frutos M, Sanz J, Martinez-Castro I, (1988) Chromatographia, 25, 861–864. The GC-MS separation and identification was performed accordingly: GC—Hewlett Packard 5890 II, MS—Hewlett Packard 5972, capillary column—Supelcowax 10, 60 m×0.25 mm, 0.15 μm film thickness, Flow—1 ml helium/min, Injection volume—1 μl cold on-column, Temperature gradient—35° C., 50° C./min to 60° C., 4° C./min to 150° C., hold for 4 min, 10° C./min to 240° C. and hold for 20 min, the NIST MS spectra library was used for substance identification. No peaks indicative for a known cGMP degradation product or off-flavor substance in substantial amounts could be detected in samples having a pH-value of less than about 6.

Additionally, also a comparison of the HPLC finger print of a freshly prepared cGMP basis composition and of the above-described samples was performed. Essentially, no changes were observed in the HPLC finger print of samples having a pH-value of less than about 6. The analytical conditions for the separation of cGMP by HPLC were the following: HPLC—Agilent 1100, Quaternary pump, diode array detector at 215 nm, injection volume—25 μl, column—TSK Gel Super ODS, 2 μm, 110A, 2×4.6 mm and 100×4.6 mm, column temperature 50° C., mobile phase—A) 0.05% trifluoric acid in water, B) 0.035% trifluoric acid in acetonitrile, flow 2.5 ml/min, solvent gradient—20% B to 40% B in 6 min, 40% B to 50% B in 1.5 min, 50% B to 95% B in 0.5 min, hold for 0.5 min, 95% B to 20% B in 1.5 min and hold for 2 min.

EXAMPLE 3

Effects of the Addition of Blocking Agent or Hydrophobic Resin on the Off-Flavor Formation 0.4 wt.-% of succinic anhydride anhydride (Merck GmbH, Darmstadt, Germany) or 2 wt.% of Serdolith III (Fluka, Buchs, Switzerland) were added to the cGMP basis composition obtained according to Example 1. Samples were taken, the pH of said samples was adjusted as described in Example 2 to a value of 6.8 respective 6.5 and said samples were stored as described in Example 2.

No off-flavor formation could be detected organoleptically (experimental proceeding, see Example 2) or via GC-MS (experimental proceeding, see Example 2) even in samples having a pH-value of of 6.8 respective 6.5, thus having a pH-value of above 6. For control, otherwise identical samples without the above-mentioned blocking agent and hydrophobic resin were prepared which had a detectable off-flavor in case of an pH-value of above 6.

EXAMPLE 4

Effects of the pH-Adjustment or the Addition of Blocking/Masking Agent or Hydrophobic Resin on the Off-Flavor Formation of Dental Care Products Containing cGMP Samples of commercially identical dental care products were taken, cGMP was added and the pH value of each of said samples was adjusted by adding either 1 M hydrochloric acid or 2 M sodium hydroxide to a pH-value in the range of between 5.0 and 7.5. All samples were stored at 49° C. for 3 weeks and were subjected subsequently to organoleptic tests.

No off-flavor was organoleptically detectable in samples having a pH-value of less than 6. During said organoleptic tests, test persons evaluated the odor of the samples adjusted to different pH-values.

In a similar experiment, 0.25 wt.-% of succinic anhydride (Merck GmbH, Darmstadt, Germany) or 0.25 wt.-% of maleic acid anhydride (Fluka, Buchs, Switzerland) or 0.1 wt.-% propio-lactone (Acros, Chemie Brunschwig, Basel, Switzerland) or 0.01 wt.-% chlorophillin or 1 wt.-% of Levatit OC 1066 (Fluka, Buchs, Switzerland) were added to the cGMP containing dental care product composition. The pH of said samples were adjusted as described in Example 2 to a value of 7.0 and said samples were stored as described in Example 2.

No off-flavor formation could be detected organoleptically (experimental proceeding, see Example 2) even in samples having a pH-value of 7.0, thus having a pH-value of above 6. For control, otherwise identical samples without the above-mentioned blocking agent and hydrophobic resin were prepared which had a detectable off-flavor in case of a pH-value of above 6.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A caseino-glycomacropeptide containing aqueous composition exhibiting a reduced off-flavor even after extended storage, comprising (i) a hydrophobic resin; and
(ii) an agent that chemically blocks functional groups in caseino-glycomacropeptide.

2. The composition according to claim 1, wherein the hydrophobic resin is selected from the group consisting of polystyrene-divinylbenzene-copolymer resin, ion exchange resin, polystyrene copolymer resin and combinations thereof.

3. The composition according to claim 1, wherein the agent is selected from the group consisting of succinic anhydride, maleic anhydride, propio-lactone, chlorophillin and derivatives thereof.

4. The composition according to claim 1, wherein the pH of the final product is in the range of from about 3 to about 7.

5. The composition according to claim 1, wherein the amount of the hydrophobic resin is in the range of from 0.01 to about 5 wt.-%, based on the final product.

6. The composition according to claim 1, wherein the amount of the agent is in the range of from 0.005 to 1 wt.-%, based on the final product.

7. The composition according to claim 1 in the form of an aqueous formulation having a water activity value between 0.2 to about 1.

8. The composition according to claim 1 in the form of a food product.

9. The composition according to claim 1, comprising a product for oral hygiene selected from the group consisting of a tooth paste, a gel, a tooth powder, a mouth wash, a chewing gum, a tablet and a lozenge.

10. A method of producing a food or oral hygiene product, the method comprising the steps of:
preparing a composition comprising caseino-glycomacropeptide, and
adding to the composition an agent that chemically blocks functional groups in caseino-glycomacropeptide and a hydrophobic resin to produce the product.

11. A method for preparing a composition for treating a disease or state chosen from the group consisting of caries, plaque formation, dental diseases, diseases of the mouth cavity, and diseases of the gums or preventing caries and/or plaque formation, the method comprising: providing a caseino-glycomacropeptide containing aqueous composition exhibiting a reduced off-flavor even after extended storage, and adding to the aqueous composition (i) a hydrophobic resin; and (ii) an agent that chemically blocks functional groups in caseino-glycomacropeptide to prepare the composition.

12. The method according to claim 11 wherein the pH of the composition is below about 7.

13. The composition according to claim 12, wherein the hydrophobic resin is selected from the group consisting of polystyrene-divinylbenzene-copolymer resin, ion exchange resin, polystyrene copolymer resin and combinations thereof.

14. The method according to claim 11, wherein the agent is selected from the group consisting of succinic anhydride, maleic anhydride, propio-lactone, chlorophillin and derivatives thereof.

15. The method according to claim 11, wherein the amount of the hydrophobic resin is in the range of from 0.05 to about 5 wt.-%, based on the final product.

16. The method according to claim 11, wherein the amount of the agent is in the range of from 0.01 to 1 wt.-%, based on the final product.

17. The method according to claim 11, wherein the amount of the hydrophobic resin is in the range of from 0.1 to about 2 wt.-%, based on the final product.

18. The method according to claim 11, wherein the amount of the agent is in the range of from 0.1 to 0.5 wt.-%, based on the final product.

19. A method of treating a disease or state chosen from the group consisting of caries, plaque formation, dental diseases, diseases of the mouth cavity, and diseases of the gums or preventing caries and/or plaque formation, the method comprising administering to an individual a therapeutically effective amount of a composition comprising caseino-glycomacropeptide, an agent that chemically blocks functional groups in caseino-glycomacropeptide and a hydrophobic resin.

20. The method according to claim 19, wherein the hydrophobic resin is selected from the group consisting of polystyrene-divinylbenzene-copolymer resin, ion exchange resin, polystyrene copolymer resin and combinations thereof.

21. The method according to claim 19, wherein the agent is selected from the group consisting of succinic anhydride, maleic anhydride, propio-lactone, chlorophillin and derivatives thereof.

22. The method according to claim 19, wherein the pH of the final product is in the range of from about 3 to about 7.

23. The method according to claim 19, wherein the amount of the hydrophobic resin is in the range of from 0.01 to about 5 wt.-%, based on the final product.

24. The method according to claim 19, wherein the amount of the agent is in the range of from 0.005 to 1 wt.-%, based on the final product.

25. The method according to claim 19, wherein the pH of the composition is below about 7.

26. The method according to claim 19, comprising a product for oral hygiene selected from the group consisting of a tooth paste, a gel, a tooth powder, a mouth wash, a chewing gum, a tablet and a lozenge.

* * * * *